United States Patent [19]

Flork

[11] Patent Number: 4,874,893

[45] Date of Patent: Oct. 17, 1989

[54] INDUSTRIAL PROCESS FOR THE PREPARATION OF AMINO ACIDS BY HYDROLYSIS OF PROTEINS IN ACID MEDIUM

[75] Inventor: Michel Flork, Chamalieres, France

[73] Assignee: Laboratoires Flork S.A. Zone Industrielle Du Brezet, Clermont-Ferrand, France

[21] Appl. No.: 133,045

[22] PCT Filed: Mar. 26, 1987

[86] PCT No.: PCT/FR87/00094

§ 371 Date: Jan. 27, 1988

§ 102(e) Date: Jan. 27, 1988

[87] PCT Pub. No.: WO87/05895

PCT Pub. Date: Oct. 8, 1987

[30] Foreign Application Priority Data

Mar. 27, 1986 [FR] France .............................. 86 04441

[51] Int. Cl.$^4$ .............................................. C07C 99/02
[52] U.S. Cl. ..................................... 562/443; 562/516
[58] Field of Search ................................ 562/516, 443

[56] References Cited

U.S. PATENT DOCUMENTS

| | | | |
|---|---|---|---|
| 2,457,117 | 12/1948 | Bernardi | 562/516 |
| 2,505,129 | 4/1950 | Manning | 562/516 |
| 2,533,114 | 12/1950 | Hoglan | 562/516 |
| 2,555,276 | 5/1951 | Pattes | 562/516 |
| 2,657,232 | 10/1953 | Borkenhagen | 562/516 |
| 3,048,627 | 8/1962 | Keil | 562/516 |

FOREIGN PATENT DOCUMENTS

56-73051  6/1981  Japan .................................. 562/516

*Primary Examiner*—James H. Reamer
*Attorney, Agent, or Firm*—Browdy and Neimark

[57] ABSTRACT

Process for the preparation of amino acids by hydrolysis of proteins such as pig bristles. Said process comprises the charging into a vat of a solution of sulphuric acid at least 12N, heating the solution to at least 100° C., adding simultaneously the proteins to be hydrolyzed and a complementary amount of sulphuric acid corresponding to the neutralization of the amine functions of the amino acids, maintaining the hydrolysis conditions in 12N medium and at 100° C., stopping the reaction by addition of water and removing the acid in excess. Thereby, a mixture of amino acids is obtained with a good yield and without degradation.

6 Claims, No Drawings

INDUSTRIAL PROCESS FOR THE PREPARATION OF AMINO ACIDS BY HYDROLYSIS OF PROTEINS IN ACID MEDIUM

The present invention relates to a new industrial process of hydrolysis of proteins for the extraction of amino-acids.

The extract of amino acids contained in proteins by hydrolysing the latter with strong inorganic acids is already known.

In order to ensure the breaking of peptide linkages of proteins and the formation of the corresponding amino acids with a good yield, it is essential that this acid has a pKA less than or equal to −2.

However, this strong acid must not bring about a degradation of the amino acids formed during the hydrolysis reaction. Some of these amino acids are unstable in a concentrated acid medium and the excess of this acid must be easy to remove from the reaction mixture after hydrolysis.

Conclusive results have been obtained in this respect in the laboratory, with aqueous solutions of hydrochloric acid, the pKA of which is −7, at a concentration of approximately 6N and at a temperature equal to or greater than 100° C.

However, an extension of these results on an industrial scale presents difficult problems because, although it is easy to remove it by distillation, at temperatures at which hydrolysis is carried out hydrochloric acid gives rise to acid vapour emissions which make it necessary to operate in an enclosed vessel and to carry out the hydrolysis of proteins in complete batches.

Thus, the low apparent density of some sources of these proteins, such as hog bristles which have an apparent density of 0.2, does not enable a large volume of these proteins to be charged into the hydrolysis reactor without excessively increasing the volume of the reactor.

Additionally, hydrochloric acid is extremely corrosive and makes it necessary to use glass-lined reactors which are particularly expensive.

The use of sulphuric acid instead of hydrochloric acid for the hydrolysis of proteins has also been proposed, especially in the patent U.S.-A-2,657,232.

However, the use of concentrated sulphuric acid does not enable a high yield of amino acids to be obtained, nor does it give a satisfactory hydrolysis, because of the degradation of some of them.

The process according to the present invention makes it possible to overcome these disadvantages, using particular conditions of hydrolysis by sulphuric acid, of which the first acidity with a pKA of −7.5 alone is sufficiently strong to cause the opening ot the peptide linkages.

The use of sulphuric acid for the hydrolysis of proteins is surprising because its second acidity is not used in the hydrolysis reaction and, a priori, it is likely to be detrimental to the stability of the amino acids as they are being formed.

Thus, it is all the more important that this acid is to be used, within the scope of the process according to the present invention, at a concentration which must be maintained throughout the period of the hydrolysis reaction at a minimum of 12N so that the dissolution of the proteins may take place and so that the hydrolysis takes place with a good yield.

It should be noted that this minimum concentration of this diacid is twice that used for hydrochloric acid.

The use of these conditions of hydrolysis with sulphuric acid according to the present invention has important consequences from an economic point of view as well as from a practical point of view.

First of all, hydrolysis in a sulphuric acid medium may be carried out in tanks containing a simple protective lining, which is a much less expensive alternative than the glass linings which are indispensable if the hydrolysis is to be carried out in a hydrochloric acid medium.

Secondly, the boiling point of a mixture of sulphuric acid with the proteins to be hydrolysed during the dissolution being only 120° C., the hydrolysis may easily be carried out at the minimum temperature of 100° C. which is required to obtain a good yield, without the emission of acid vapours, unlike in the case of hydrochloric acid.

Finally and most importantly, as the hydrolysis reaction with sulphuric acid may be carried out under conditions of exposure to air, it will be possible to introduce gradually into the tank the volume of proteins to be hydrolysed and also to introduce gradually the quantity of sulphuric acid which will be consumed during the hydrolysis reaction.

Such a procedure, which involves the gradual addition of proteins and of the acid into the reaction medium, either continuously or by successive additions, enables the sulphuric acid concentration to be maintained within a narrow range throughout the period of hydrolysis, which improves the yield of amino acids.

In fact, under these conditions, a sufficient dissociation of the peptide linkages is obtained, the hydrolysis reaction being controlled at the same time so as to avoid any degradation of the amino acids produced.

The process according to the present invention consists in charging previously into a tank an aqueous solution of sulphuric acid of concentration at least equal to 12N, heating the solution to a temperature of at least 100° C., adding simultaneously the proteins and an additional amount of sulphuric acid corresponding to that required for the neutralization of amine groups of amino acids originating from the hydrolysis of the proteins, continuing the hydrolysis reaction while maintaining the sulphuric acid concentration at least at 12N and the temperature at least at 100° C., stopping the hydrolysis by adding water so as to lower the temperature and to reduce the sulphuric acid concentration to a value of not more than 6N and removing the excess sulphuric acid.

Because sulphuric acid is used, it is no longer essential to work in a closed vessel and to introduce into the tank right from the beginning of the reaction the entire amount of raw materials required for protein hydrolysis.

On the contrary, only a part, of the order of from 40 to 60% by weight, of the total amount of sulphuric acid used in the reaction is introduced initially into the hydrolysis tank.

Next, after heating to the required temperature, the proteins to be hydrolysed and the additional amount of sulphuric acid corresponding to the neutralization of the amine groups are then introduced into the tank, preferably simultaneously, the rates of addition being adjusted firstly by regulating the absolute volumes of proteins and additional sulphuric acid added into the tank in order to ensure a temperature which remains as constant as possible and secondly by regulating the relative volumes of these two ingredients thus added, in order to maintain the concentration of sulphuric acid substantially at the initial level.

This spreading over a period of time of the introduction of the raw materials required for hydrolysis, which would not have been possible in a hydrochloric acid medium, is an important feature of the process according to the preferred embodiments of the present invention.

First of all, it enables the acidity to be kept much more constant throughout the period of hydrolysis reaction, it being possible for the acid concentration to be maintained at from 12N to 14N so as to avoid any degradation of amino acids, whereas if the entire amount of raw material were to be charged initially, it would be necessary to start with a mixture of which the acid concentration would be from 20N to 25N.

It also enables a much larger volume of proteins for hydrolysis to be introduced into a tank of a given volume as these proteins are dissolved as and when they are introduced.

Finally, it enables the conversion of the amino acids into other amino acids or their racemization with the formation of the dextrorotatory form instead of the laevorotatory form to be avoided.

Thus, the dissolution of proteins, hydrolysis of their peptide linkages and neutralization of amino acids take place simultaneously, these different reactions taking place at their own individual rates, which vary depending on the different amino acids concerned.

The proteins used as raw materials for the process according to the invention may be of animal or vegetable origin, each as hair keratin, hair or feathers of animals, hog bristles from slaughterhouses being the preferred protein source.

In order to obtain a good yield, even with large quantities of proteins, the reaction mixture is maintained stirred at a temperature preferably of 105° C. for a period sufficient to enable the proteins to dissolve and to be hydrolysed in the sulphuric acid bath.

When the hydrolysis is virtually complete, the hydrolysis process is topped by injecting water so as to lower the temperature to approximately 60° C. and to reduce the sulphuric acid concentration from 12N to a value of not more than 6N. The secondary reactions which give rise to degradation of amino acids and to losses in yield are thereby avoided.

The final step in the process consists in removing the excess sulphuric ions and the various organic substances, colorants and fatty substances so as to obtain a hydrolysate suitable for the isolation and purification of the dissolved amino acids it contains.

In a preferred embodiment of the invention, the sulphuric ions are precipitated in the form of calcium sulphate by adding slaked lime so as to restric heat evolution and carbon dioxide evolutions. This is preferably carried out at a pH of from 1 to 2 in a cooled, jacketed reactor. This precipitation is carried out by stirring, in a relatively short period of time, of the order of from 2 to 4 hours, in order to prevent the particles of lime from not being completely converted to calcium sulphate, the crystallization of calcium sulphate on the particles of lime making it possible to increase the particle size of the precipitate and to facilitate its subsequent separation. During this precipitation, the fatty acids are entrained by adsorption on the sulphates.

The separation of the calcium sulphate precipitate is carried out by decanting or filtering.

The invention will now be illustrated using an example of industrial-scale implementation which is not intended to limit the scope of the present invention.

EXAMPLE

A 50 $m^3$ tank made of standard-grade steel, internally coated with hypalon (trademark), is charged with 8.5 cubic meters of water. This is heated with hot steam until the temperature rises to a temperature of from 90° C. to 100° C., which brings in an additional amount of water of 2.1 $m^3$, and 5.7 $m^3$ of 92% sulphuric acid, with a density of 1.83, is poured in rapidly, with stirring, which causes the temperature to rise to from 105° to 110° C.

Subsequently, 15 tonnes of hog bristles are introduced into the tank, at a rate of approximately 2.250 tonnes per hour, pouring in, at the same time, an additional amount of 92% sulphuric acid at a rate of 1 cubic meter per hour.

After having maintained the temperature at from 105° to 110° C. and having continued the stirring for 4 hours from the time of completing the introduction of the 15 tonnes of bristles and of 6.67 cubic meters of acid, the hydrolysis is stopped by adding from 20 to 25 $m^3$ of water into the tank, the stirring being continued.

Neutralization is then carried out by pouring the hydrolysis liquid into a reactor, in fractions of 5 $m^3$ each, to which 2 $m^3$ of water are added and 1300 kg of slaked lime are dusted in slowly.

Each of these fractions of hydrolysis liquid is stirred for 2 hours, avoiding the formation of foam, maintaining the temperature below 50° C. and ensuring that the pH reaches a value of from 1.5 to 2. Finally, the liquid is poured into a settling tank.

The neutralization operation is repeated 10 times to empty the hydrolysis tank completely, which corresponds to a consumption of 13,000 kg of slaked lime for approximately 50 $m^3$ of hydrolysis liquid.

After pouring into the settling tank, a foam of variable size and which is stable may be formed at the surface.

It is then advisable to spray the surface of the tank with a jet of water in order to destroy the foam.

Settling is allowed to proceed overnight and the clear hydrolysis liquid is recovered. This liquid contains, on average, after the hydrolysis of 13 tonnes of hog bristles, 12,500 kg of total amino acids, including the following, in particular:

750 kg of aspartic acid
650 kg of threonine
1350 kg of serine
1900 kg of glutamic acid
900 kg of proline
650 kg of glycine
600 kg of alanine
800 kg of valine
1150 kg of cystine
100 kg of methionine
550 kg of isoleucine
1100 kg of leucine
400 kg of tyrosine
450 kg of phenylalanine
650 of lysine
250 of histidine and
1200 kg of arginine.

The above example and the considerations which precede do not limit in any way the scope of the present invention, which relates to any industrial process for the hydrolysis of proteins for extracting amino acids in which one or more of the following claims are employed.

What is claimed is:

1. In a process for the industrial preparation of amino acids by hydrolysis of protein of animal or vegetable origin in a sulfuric acid medium within a reaction tank, comprising:

conducting protein hydrolysis with sulfuric acid having a concentration of at least 12N and at a temperature of at least 100° C., stopping the hydrolysis by addition of water so as to lower the temperature and to reduce the sulfuric acid concentration to a value of 6N or less and removing the excess of sulfuric acid by neutralization, the improvement wherein the reaction tank is charged with water and an initial portion of a sulfuric acid solution in an amount necessary for said hydrolysis of said protein, said tank is heated at a temperature between 100° C. and the boiling point thereof prior to the addition of said protein to said tank, said water diluting the sulfuric acid solution initially added, so that the concentration of sulfuric acid within said reaction tank is about 12-14N, the protein to be hydrolyzed is then added simultaneously with but separately from a remaining portion of said sulfuric acid solution in an amount necessary for said hydrolysis in an amount corresponding to that required for the neutralization of amine groups of amino acids generated by the hydrolysis of the protein, so that said protein and said remaining portion of said sulfuric acid solution are added at independently adjustable rates while maintaining the concentration of acid with said reaction tank at about 12-14N.

2. Process according to any one of claim 1 characterized in that the proportion of acid charged previously into the tank prior to the introduction of the proteins is from 40 to 60% by weight relative to the total amount of sulphuric acid used in the hydrolysis reaction.

3. Process according to any foregoing claim 2, characterized in that the excess sulphuric acid is removed after hydrolysis by adding slaked lime and decanting the calcium sulphate precipitate.

4. Process according to claim 3, characterized in that the addition of slaked lime is carried out while being stirred at a temperature not exceeding 50° C. until a pH of from 1 to 2 is obtained.

5. The process of claim 1, wherein said protein is selected from the group consisting of hair keratin, animal feathers and hog bristles.

6. The process of claim 5, wherein said protein is hog bristles.

* * * * *